United States Patent
Colston et al.

(10) Patent No.: US 6,175,669 B1
(45) Date of Patent: Jan. 16, 2001

(54) OPTICAL COHERENCE DOMAIN REFLECTOMETRY GUIDEWIRE

(75) Inventors: Billy W. Colston, Livermore; Matthew Everett, Pleasanton; Luiz B. Da Silva, Danville; Dennis Matthews, Moss Beach, all of CA (US)

(73) Assignee: The Regents of the Universtiy of California, Oakland, CA (US)

( * ) Notice: Under 35 U.S.C. 154(b), the term of this patent shall be extended for 0 days.

(21) Appl. No.: 09/050,571

(22) Filed: Mar. 30, 1998

(51) Int. Cl.[7] .................................................... G02B 6/00
(52) U.S. Cl. ........................ 385/12; 385/24; 385/116; 356/359
(58) Field of Search .................................. 385/12, 13, 51, 385/15, 24, 115–119; 356/357–360, 117; 378/51

(56) References Cited

U.S. PATENT DOCUMENTS

| | | | |
|---|---|---|---|
| 5,212,586 | * 5/1993 | Van Delden | 359/281 |
| 5,268,741 | * 12/1993 | Chou et al. | 356/351 |
| 5,321,501 | * 6/1994 | Swanson et al. | 356/345 |
| 5,453,827 | * 9/1995 | Lee | 356/73.1 |
| 5,459,570 | * 10/1995 | Swanson et al. | 356/345 |
| 5,491,524 | * 2/1996 | Hellmuth et al. | 351/212 |
| 5,835,642 | * 11/1998 | Gelikonov et al. | 385/4 |
| 5,901,261 | * 5/1999 | Wach | 385/38 |
| 5,911,017 | * 6/1999 | Wach et al. | 385/12 |

FOREIGN PATENT DOCUMENTS

| | | |
|---|---|---|
| 0484913 | 5/1992 | (EP) . |
| 0 812 566 A2 | * 4/1997 | (EP) . |
| WO 97/32182 | 9/1997 | (WO) . |

OTHER PUBLICATIONS

Hee et al., Polarization –sensitive low–coherence reflectometer for birefringence characterization and ranging, Journal of Optical Society of America B, vol. 9, No. 6, pp. 903–908, Jun. 1992.*

Tearney et al., "Scanning single–mode fiber optic catheter–endoscope for optical coherence tomography", Optics Letters vol. 21, No. 7, p. 543–545, Apr. 1, 1996.*

Hee et al., "Polarization–sensitive low–coherence reflectometer for birefringence characterization and ranging", Journal of Optical Society of America B, vol. 9, No. 6, p. 903–908, Jun. 1992.*

* cited by examiner

Primary Examiner—John D. Lee
Assistant Examiner—Michelle R. Connelly-Cushwa
(74) Attorney, Agent, or Firm—John P. Wooldridge; Alan H. Thompson (57) ABSTRACT

A guidewire with optical sensing capabilities is based on a multiplexed optical coherence domain reflectometer (OCDR), which allows it to sense location, thickness, and structure of the arterial walls or other intra-cavity regions as it travels through the body during minimally invasive medical procedures. This information will be used both to direct the guidewire through the body by detecting vascular junctions and to evaluate the nearby tissue. The guidewire contains multiple optical fibers which couple light from the proximal to distal end. Light from the fibers at the distal end of the guidewire is directed onto interior cavity walls via small diameter optics such as gradient index lenses and mirrored corner cubes. Both forward viewing and side viewing fibers can be included. The light reflected or scattered from the cavity walls is then collected by the fibers, which are multiplexed at the proximal end to the sample arm of an optical low coherence reflectometer. The guidewire can also be used in nonmedical applications.

23 Claims, 7 Drawing Sheets

OPTICAL COHERENCE DOMAIN REFLECTOMETRY GUIDEWIRE

The United States Government has rights in this invention pursuant to Contract No. W-7405-ENG48 between the United States Department of Energy and the University of California for the operation of Lawrence Livermore National Laboratory.

BACKGROUND OF THE INVENTION

The invention relates generally to guidewires for medical procedures and more particularly to guidewires with optical sensing capabilities.

Optical coherence domain reflectometry (OCDR) is a technique developed by Youngquist et al. in 1987 (Youngquist, R. C. et al., "Optical Coherence-Domain Reflectometry: A New Optical Evaluation Technique," 1987, Optics Letters 12(3):158–160). Danielson et al. (Danielson, B. L. et al., "Guided-Wave Reflectometry with Micrometer Resolution," 1987, Applied Physics 26(14): 2836–2842) also describe an optical reflectometer which uses a scanning Michelson interferometer in conjunction with a broadband illuminating source and cross-correlation detection. OCDR was first applied to the diagnosis of biological tissue by Clivaz et al. in January 1992 (Clivaz, X. et al., "High-Resolution Reflectometry in Biological Tissues," 1992, Optics Letters 17(1):4–6). A similar technique, optical coherence tomography (OCT), has been developed and used for imaging with catheters by Swanson et al. in 1994 (Swanson, E. A. et al., U.S. Pat. Nos. 5,321,501 and 5,459,570). Tearney et al. (Tearney, G. J. et al., "Scanning Single-Mode Fiber Optic Catheter-Endoscope for Optical Coherence Tomograph," 1996, Optics Letters 21(7):543–545) also describe an OCT system in which a beam is scanned in a circumferential pattern to produce an image of internal organs. U.S. Pat. No. 5,570,182 to Nathel et al. describes method and apparatus for detection of dental caries and periodontal disease using OCT. However, as OCT systems rely on mechanical scanning arms, miniaturizing them enough to operate on a guidewire would be very difficult.

Polarization effects in an OCDR system for birefringence characterization have been described by Hee et al. (Hee, M. R. et al., "Polarization-sensitive low-coherence reflectometer for birefringence characterization and ranging," J. Opt. Soc. Am. B, Vol. 9, No. 6, June 1992, 903–908) and in an OCT system by Everett et al. (Everett, M. J. et al., "Birefringence characterization of biological tissue by use of optical coherence tomography," Optics Letters, Vol. 23, No. 3, Feb. 1, 1998, 228–230).

Figure 1:
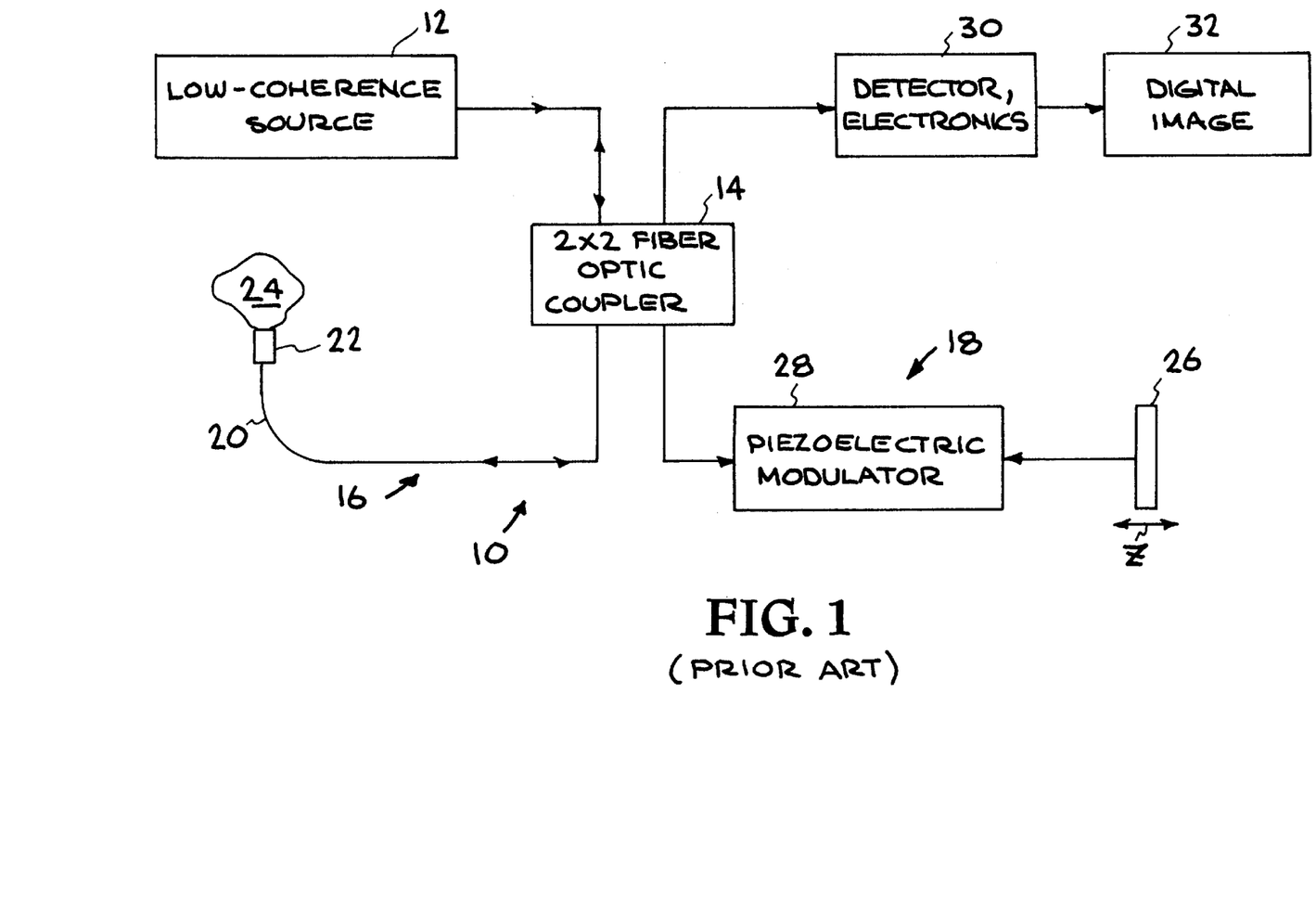
FIG. 1 is a prior art OCDR scanning system.

In a prior art OCDR scanning system 10, shown in FIG. 1, light from a low coherence source 12 is input into a 2×2 fiber optic coupler 14, where the light is split and directed into sample arm 16 and reference arm 18. An optical fiber 20 is connected to the sample arm 16 and extends into a device 22, which scans an object 24. Reference arm 18 provides a variable optical delay. Light input into reference arm 18 is reflected back by reference mirror 26. A piezoelectric modulator 28 may be included in reference arm 18 with a fixed mirror 26, or modulator 28 may be eliminated by scanning mirror 26 in the Z-direction. The reflected reference beam from reference arm 18 and a reflected sample beam from sample arm 16 pass back through coupler 14 to detector 30 (including processing electronics), which processes the signals by techniques that are well known in the art to produce backscatter profile (or "image") on display 32.

SUMMARY OF THE INVENTION

This invention is a guidewire with sensing capabilities based on a multiplexed optical coherence domain reflectometer (OCDR), which allow it to sense location, thickness, and structure of the arterial walls or other intra-cavity regions as it travels through the body during minimally invasive medical procedures. This information will be used both to direct the guidewire through the body by detecting vascular junctions and to evaluate the nearby tissue. The guidewire contains multiple optical fibers which couple light from the proximal to distal end. Light from the fibers at the distal end of the guidewire is directed onto interior cavity walls via small diameter optics, such as gradient index lenses and mirrored corner cubes. The light reflected or scattered from the cavity walls is then collected by the fibers which are multiplexed at the proximal end to the sample arm of an optical low coherence reflectometer. The resulting data, collected sequentially from the multiple fibers, provides information about branching of arteries necessary for guiding the guidewire through the arterial system. It also can be used to locate small structural abnormalities in the arterial or cavity wall (such as aneurysms or arteriovenous malformations) that are currently not resolvable by existing techniques. The guidewire can also be used in nonmedical applications.

By multiplexing between a number of sensor fibers with an optical switch, the OCDR system of the invention has multiple sequentially accessed sensor points consisting of the tip of each multiplexed fiber. These sensor points measure the scattering of light as a function of distance from the fiber tip, thus determining both the distance between the fiber tip and the nearest tissue and any structure in that tissue. For guiding purposes, a number of these fibers are embedded in the guidewire with their tips at the distal end of the guidewire. Miniature collimating and reflection optics deflect the light from the fiber tips toward the vascular walls, thus sensing any branching of the vasculature or abnormalities in the walls.

DETAILED DESCRIPTION OF THE INVENTION

The invention uses a multiplexed optical coherence domain reflectometer in a guidewire as an aid in guiding the wire during minimally invasive medical procedures or in nonmedical in situ probes.

Figure 2A:
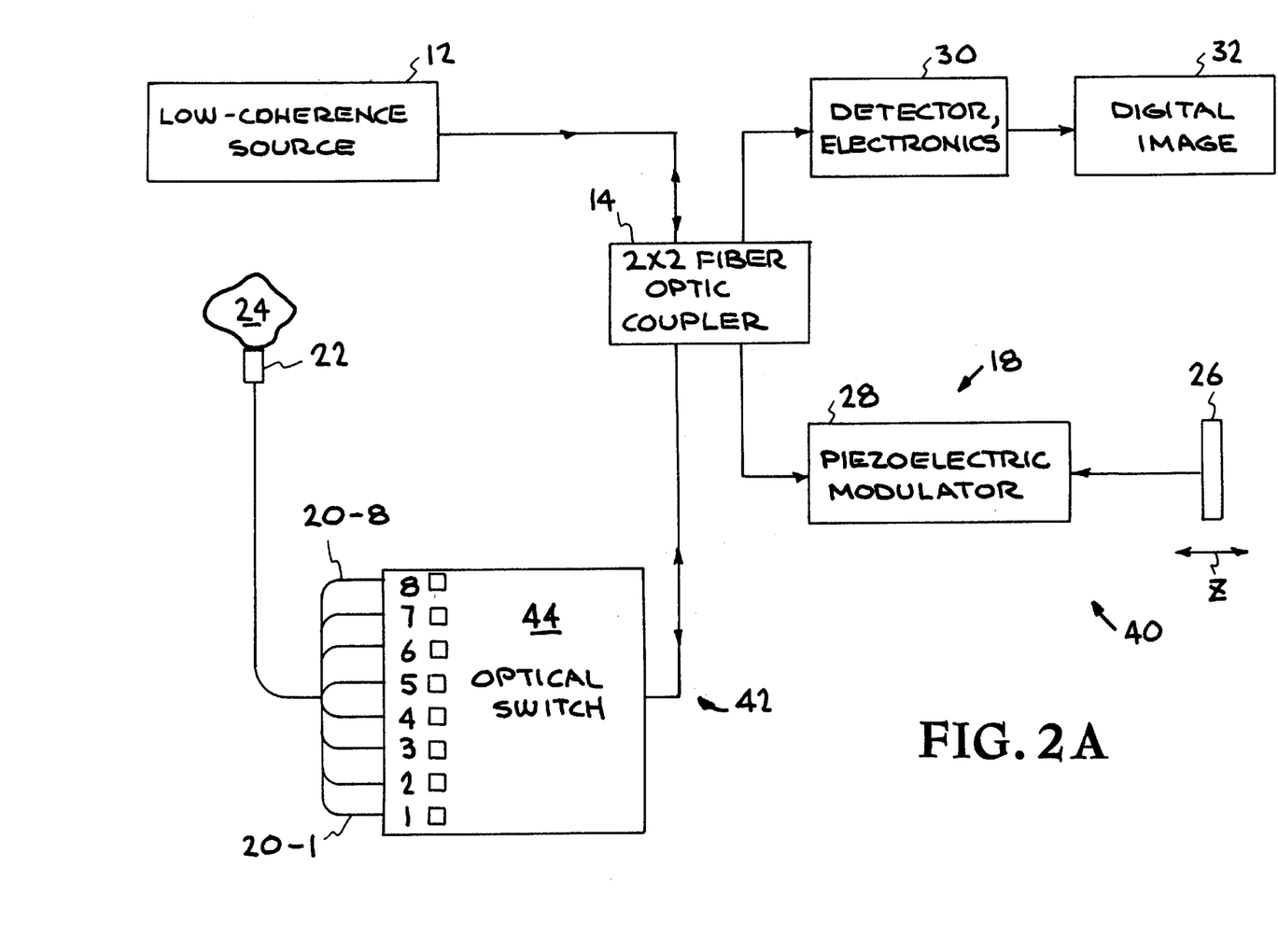
FIG. 2A is a schematic diagram of an OCDR guidewire optical sensing system with multiplexed sample arm.

The guidewire optical sensing system 40 is illustrated in FIG. 2A. The device is based on an optical coherence domain reflectometer (OCDR) which has been multiplexed. Except for the multiplexed feature, the system is similar to the prior art system 10 of FIG. 1. Output from a low coherence light source 12 is split at the 2×2 fiber optic coupler 14 and directed through a multiplexed sample arm 42 toward the sample 24 and through a reference arm 18 to reference mirror 26. Reflections from the mirror 26 and backscattered light from the sample 24 are recombined at the coupler 14 and propagated to the detector 30 (and light source 12). Constructive interference creates a signal at the detector 30 when the sample and reference reflections have traveled approximately the same optical group delay. The shorter the coherence length of the source, the more closely the sample and reference arm group delays must be matched for constructive interference to occur. By imposing a changing optical delay in the reference arm 18 with a known velocity, either by scanning mirror 26 in the Z-direction or with a piezomodulator 28 (with fixed mirror 26), the amplitudes and longitudinal positions of reflections from the sample 24 can be measured with high precision. The sample arm 42 contains a multiplexer 44 for switching between several (e.g., 8) fibers, 20-1 . . . 20-8, allowing sequential spatially distinct regions to be diagnosed consecutively using the same basic OCDR system. The fibers can be placed anywhere in the guidewire. Some fibers can be forward viewing and some can be side viewing.

Figure 2B:
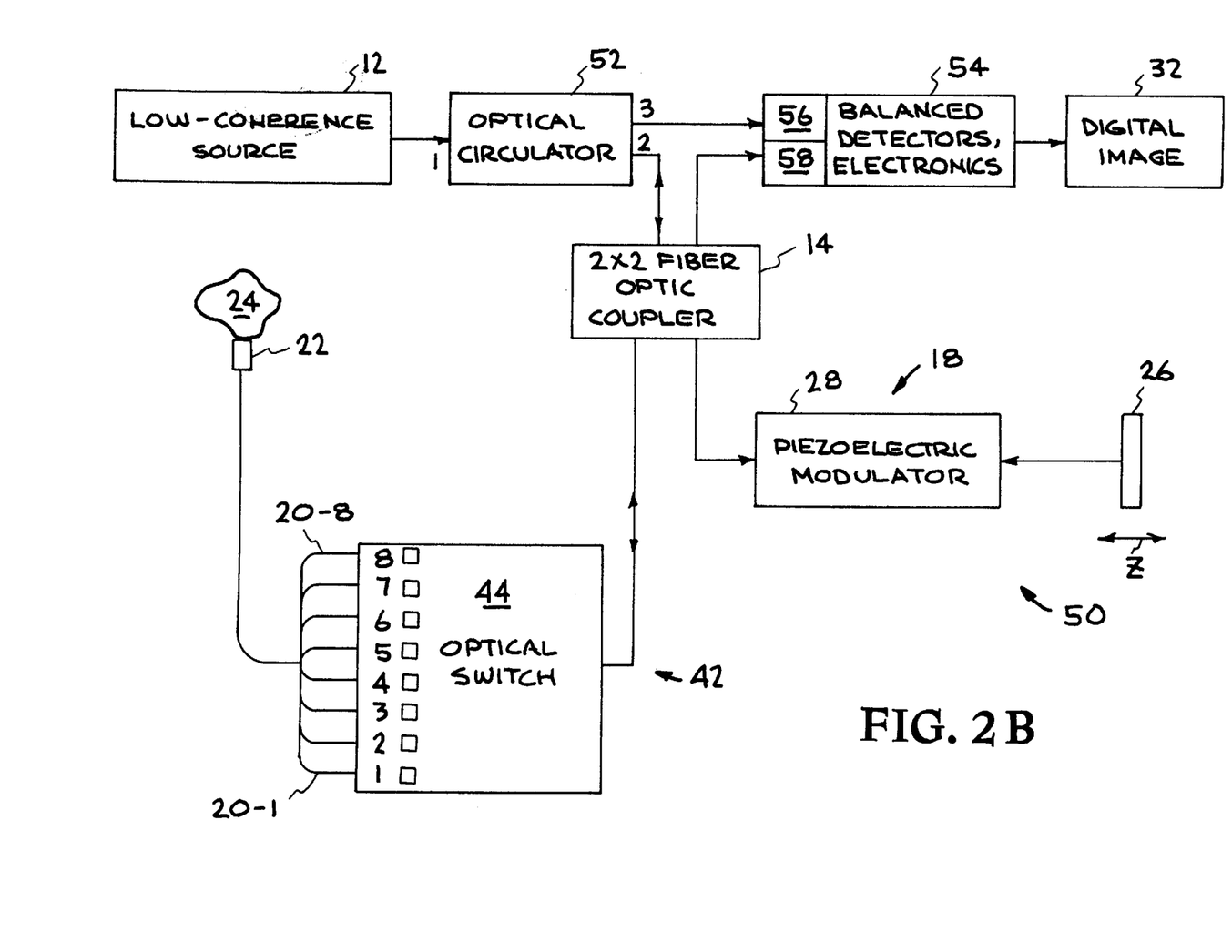
FIG. 2B is a schematic diagram of an OCDR guidewire optical sensing system with a multiplexed sample arm and optical circulator.

An alternate embodiment, guidewire optical sensing system 50, is shown in FIG. 2B. Guidewire sensing system 50 is similar to guidewire sensing system 40 of FIG. 2A, except that an optical circulator 52 is added to the system and detector 30 is replaced by balanced detector unit 54. Balanced detector unit 54 includes a pair of detectors 56, 58 with associated processing electronics, and produces a backscatter profile on display 32.

OCDR/OCT systems are based on white light Michelson interferometers, in which light from a source is split via a beamsplitter into two arms, a reference arm and a sample arm. Light is then reflected back to the beamsplitter in both arms. The light returning to the beamsplitter is then split, half returning to the source and the rest going to a detector. The light returning to the source is wasted and can cause the source to lase, reducing the bandwidth of the source.

The optical circulator 52 has three ports, as shown in FIG. 2B. The first port is connected to the output of source 12 and the second port is connected to coupler 14. Thus light from source 12 passes through optical circulator 52 to coupler 14 and into reference arm 18 and multiplexed sample arm 42, as before. In system 40 of FIG. 2A, the light returning to coupler 14 from reference and sample arms 18, 42 would be split, with some going to detector 30, where useful information is obtained, and some going back to source 12. In system 50 of FIG. 2B, some of the light passing back through coupler 14 goes to detector unit 54 and some goes back to the second port of optical circulator 52. But light returning to the second port of optical circulator 52 cannot pass back through the first port to source 12. Instead the light passes through the third port to detector unit 54.

Thus putting an optical circulator 52 in the source arm between source 12 and coupler 14 allows the light that would have returned to the source 12 to be sent to another detector. Detector unit 54 contains a pair of balanced detectors 56, 58. Detector 58 receives the light which passes directly from coupler 14 while detector 56 receives the light which passes back through optical circulator 52. Thus detector unit 54 can utilize all the reflected light. In the balanced detection scheme, the signal on the second detector is subtracted from the first. The signal caused by heterodyning between light in the reference and sample arms is 180 degrees out of phase on the two detectors.

The use of optical circulator 52 provides three benefits: (1) it protects source 12 from optical back reflections which can cause it to lase; (2) it allows detector unit 54 to collect twice as much light, enhancing system sensitivity; (3) balanced detection is achieved by subtracting the signal on one detector from the other which eliminates source or ring noise as fluctuations in source intensity appear equally on both detectors and thus cancel when the two signals are subtracted.

Figure 2C:
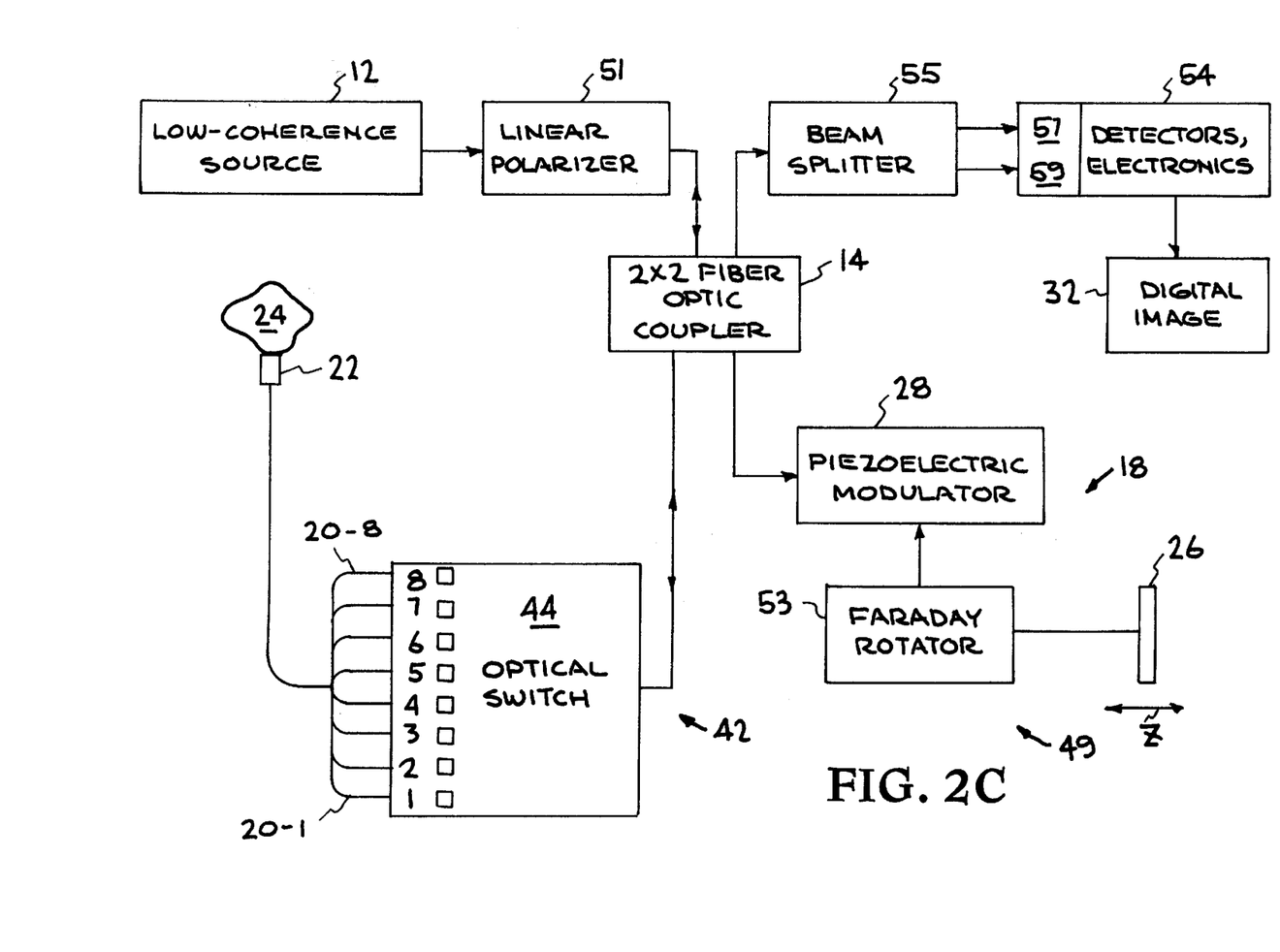
FIG. 2C is a schematic diagram of an OCDR guidewire optical sensing system with multiplexed sample arm using polarized light.

Another embodiment, guidewire optical sensing system 49, is shown in FIG. 2C. Guidewire sensing system 49 is similar to guidewire sensing system 40 of FIG. 2A, except that the polarization of the light through the system is controlled by polarization maintaining (PM) fibers and optics. Mismatches between the polarization states of the light returning from the reference and sample arms 42, 18 in system 40 causes reduction in the coherent interference between light from the two arms and thus losses of signal. Control of the polarization state of the light in the system can both eliminate losses in signal due to depolarization of the light and provide the additional capability of measurement of the birefringence of the sample 24. In this embodiment, linearly polarized light is introduced into the system either through use of a linearly polarized broadband light source 12 or by placing linear polarizer 51 directly after an unpolarized source 12. The linear polarization of the light is then maintained through the use of PM fibers and a PM fiber optic coupler 14 where the linear polarization is one of the two modes of the PM fiber and PM coupler 14. The polarization state of the light returning from the reference arm 18 is modified by either a waveplate or faraday rotator 53 so as to be equally split between the two modes (orthogonal polarizations) of the PM fiber. A polarization beam splitter 55 in the detector arm splits the two polarizations and directs them to two separate detectors 57, 59 of detector unit 54. In one embodiment, the optical fibers 20-1 . . . 20-8 in the sample arm 42 are not polarization maintaining. In this case, the polarization beam splitter 55 ensures that the polarization state of the light from the reference and sample arms 42, 18 is matched on each detector 57, 59, thus eliminating the losses due to depolarization of the light. The light returning from the sample arm 42 is then measured by summing the signals from the two detectors 57, 59. In another embodiment, the optical fibers 20-1 . . . 20-8 in the sample arm 42 are polarization maintaining. The fibers 20-1 . . . 20-8 can be oriented such that the light leaving the fibers is linearly polarized at an angle approximately 45° relative to the fast axis of birefringence of the sample 24. Alternatively a quarter waveplate 85 (shown in FIG. 4B) can be placed at the distal end of each fiber 2-1 . . . 20-8 to cause the light entering the sample to be circularly polarized. In either case, the total light in all polarization states returning from the sample 24 is once again determined by summing the signal from the two detectors 57, 59. In addition, detector unit 54 includes means for ratioing the output signals from detectors 57, 59; the birefringence of the sample 24 is determined based on the arc tangent of the ratio of the signals from the two detectors 57, 59.

As previously described, a variable optical delay can be produced in reference arm 18 by scanning reference mirror 26 back and forth in the Z-direction (see FIGS. 1, 2A–B). However, there are two key issues in varying the axial length of the reference arm: linearity of the axial scan and duty cycle.

Figure 3A:
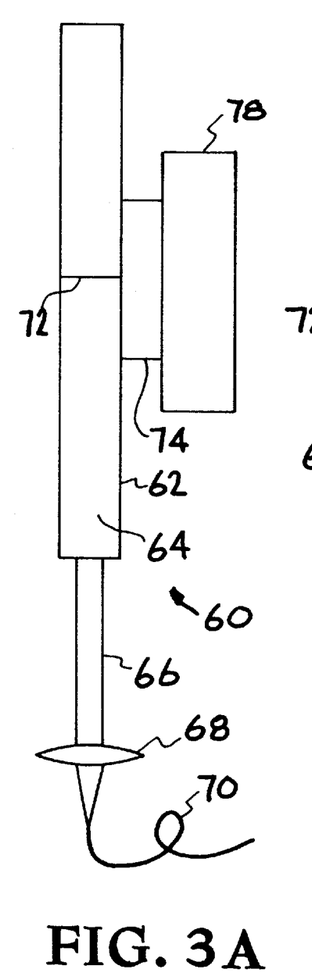
FIGS. 3A, B are side and top views of a rotating helix reference mirror.
Figure 3B:
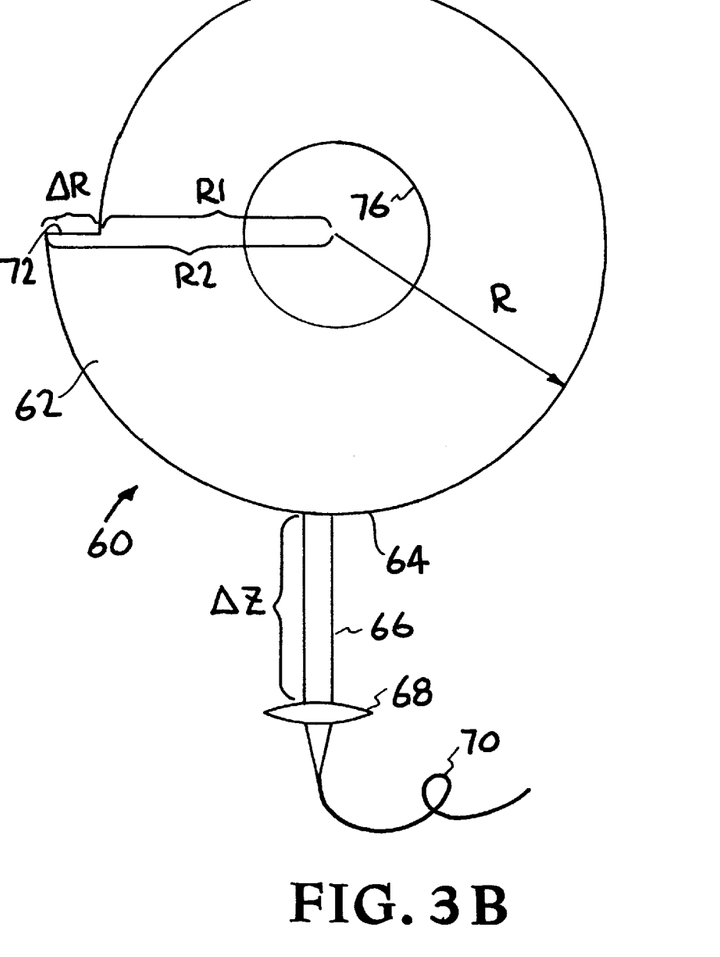

A rotating helix reference mirror 60, shown in FIGS. 3A, B, can be used to smoothly vary the path length in the reference arm of the OCDR system. Mirror 60 is formed of a disk 62 with a radius R which varies from R1 to R2 over its entire circumference. Lateral edge surface 64 of disk 62 is a highly reflective mirror so that a collimated light beam 66 incident thereon at normal incidence will be reflected back. Collimated light beam 66 is formed by collimating the diverging light from optical fiber 70 which forms the reference arm of the OCDR system. Lens 68 is used to collimate the output of fiber 70. When the beam is reflected back by surface 64, lens 68 focuses the light back into fiber 70.

When mirror 60 is positioned so that beam 66 is incident on point 72, at which the radius R=R2, the longest radius, the path length ΔZ between lens 68 and surface 64 is the shortest. As mirror 60 is rotated about shaft 74, which fits into central opening 76 and is turned by motor 78, the path length ΔZ increases as R decreases. As mirror 60 completes an entire 360 degree revolution, R=R1, the shortest radius, is reached and ΔZ has increased by ΔR=R2−R1. Beam 66 then returns to point 72 and starts a new cycle. In each cycle, the path length ΔZ changes by ΔR, or the optical path length change in the reference arm AL changes by 2ΔZ=2ΔR=2(R2−R1). Disk 62 can typically be about 2 inches in diameter and 0.2 inches thick, with a ΔR of about 0.2 inches. Thus the optical path length will be varied by about half an inch on each cycle.

Figure 4A:
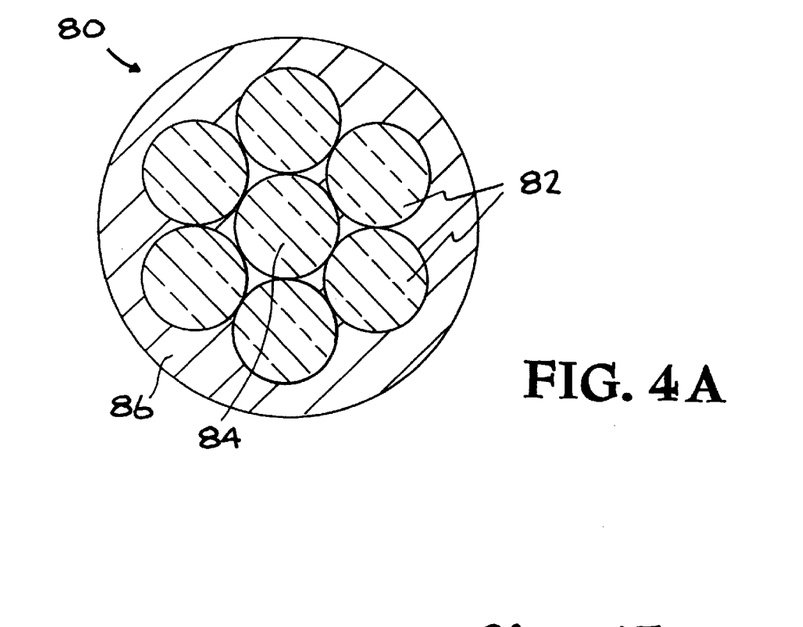
FIGS. 4A, B are sectional and side views of an OCDR optical sensing guidewire.
Figure 4B:
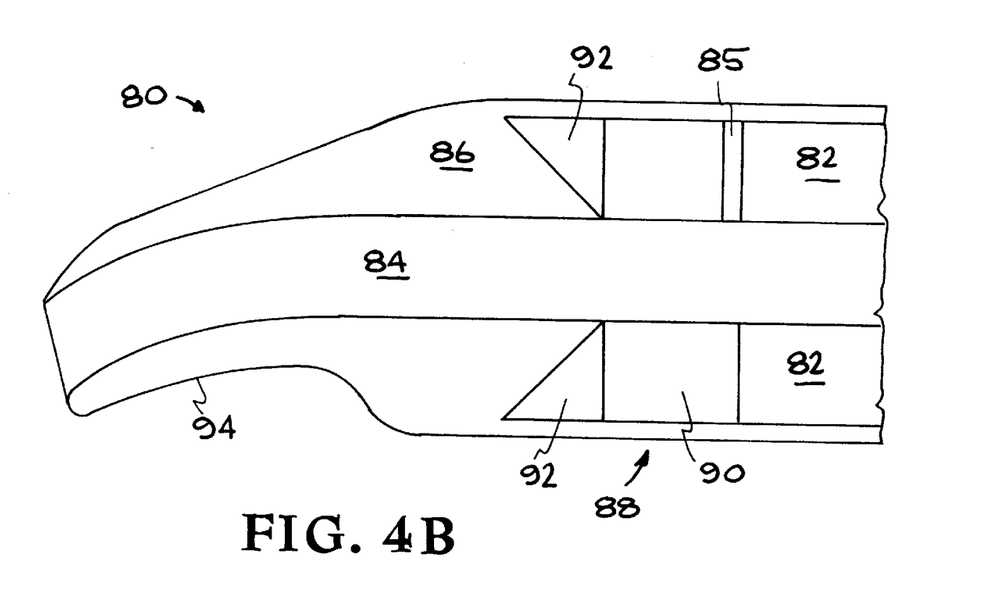

As shown in FIGS. 4A, B, the guidewire 80 consists of a plurality (e.g., seven) of optical fibers, including peripheral fibers 82 and a central fiber 84 embedded in a guidewire body 86 of x-ray blocking material. The number of fibers in the guidewire is dependent on the limit of the guidewire diameter and requirements for flexibility, the fiber optic diameter, and the desired speed of acquisition. Either single or multiple mode optical fibers can be used. Single mode fibers are preferable for maximizing the longitudinal resolution. However, multimedia fibers can be made smaller, thus minimizing the guidewire's size and maximizing its flexibility. Average sizes for single mode fibers are on the order of 100 μm diameter. Thus seven fibers, as shown in FIG. 4A, would lead to a guidewire approximately 400 microns in diameter (including 50 microns of x-ray absorbing material around the fibers). Miniature optics 88 (GRIN lenses 90 and mirrored corner cubes 92, for instance) can be used for collimating and directing the light emerging from the fiber tips of the peripheral fibers onto the adjacent arterial or cavity wall. The optical elements 88 extend through guidewire body 86 to allow light to be transmitted to and received from the surrounding area. The x-ray absorber provides conventional radiographs of the guidewire position while the central optical fiber 84 scans ahead and the peripheral optical fibers 82 scan to the sides of the device. Preferably, the tip 94 of this device is somewhat elongated to allow easier navigation of bends in the circulatory pathways. The central fiber extends into tip 94 and looks directly ahead.

Miniature optics 88 can be eliminated and just the bare fiber tip can be used, as with central fiber 84; different combinations of optical elements, e.g. GRIN lens 90 without corner cube 92 or corner cube 92 without GRIN lens 90, can also be used. Thus with different optical arrangements, foreward and/or side viewing can be obtained.

Figure 5A:
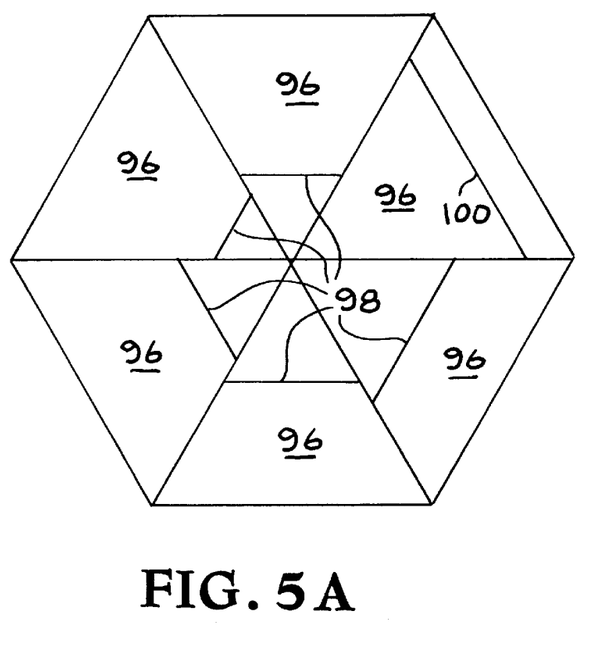
FIGS. 5A, B are displays generated by the guidewire sensing system.
Figure 5B:
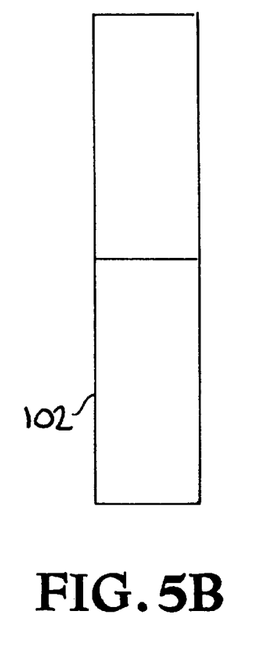

The scan data can be displayed, as shown in FIGS. 5A, B, as a radial pie slice 96 for each sideways looking fiber and a separate plot 102 for the forward looking fiber. As seen in FIG. 5A, each segment 96 is a scan obtained by one of the side viewing fibers, which have been multiplexed to produce a 360 degree view. The boundaries 98 represent the artery walls. Since there are only a discrete number of fibers and sectors 96, there are some discontinuities in the boundaries 98. However, boundary 100 is clearly much farther away and represents a junction with a secondary artery.

Figure 6:
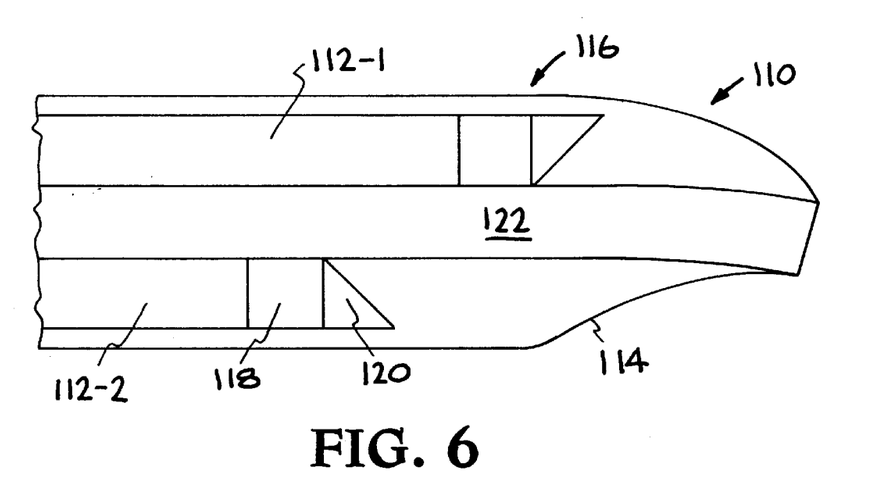
FIG. 6 shows a guidewire with OCDR scanning fibers at various positions along its length.

A guidewire device 110 as shown in FIG. 6 may have a plurality of peripheral fibers, e.g. fibers 112-1, 112-2, embedded in guidewire body 114 with individual fibers extending to different lengths along the body 114. Each fiber may terminate in optical elements 116, e.g. GRIN lens 118 and corner cube 120, for side viewing, or some of the fibers can be forward viewing, as central fiber 122 which extends ahead of fiber 112-1. Thus features found a different locations along the length of the catheter can be viewed without moving the guidewire.

Applications for the invention include any method or procedure where accurate guidewire positioning is beneficial, including angioplasty, stroke treatment, aneurysm, arteriovenous malformations, ophthalmic surgery, laparoscopic surgery, arthroscopic surgery, treatment of colorectal disorders, sinus disorders, ear surgery, pneumothoracic surgery, spinal surgery, bladder surgery, esophageal surgery, uteral disorders, and essentially any treatment that requires accurate information about tissue structures while using a guidewire inside a body cavity. In addition to medical applications, the invention can be used for nonmedical instruments which are to be used to inspect and probe in situ locations.

Changes and modifications in the specifically described embodiments can be carried out without departing from the scope of the invention, which is intended to be limited only by the scope of the appended claims.

What is claimed is:

1. A guidewire optical sensing apparatus, comprising:
    a plurality of single mode optical fibers, each fiber having a distal and proximal end;
    a body of x-ray absorbing material surrounding the fibers and forming a flexible guidewire with embedded fibers, the fibers directing light transmitted through the fiber to a surrounding area and collecting light reflected back from the surrounding area;
    an optical coherence domain reflectometer (OCDR); and
    a multiplexer connecting the OCDR to the proximal ends of the fibers to sequentially switch to each of the fibers.

2. The apparatus of claim 1 wherein the plurality of fibers comprises a central fiber positioned in the center of the guidewire and a plurality of peripheral fibers positioned around the periphery of the guidewire.

3. The apparatus of claim 2 further comprising optical elements connected to the distal ends of at least some of the fibers and extending through the body of x-ray absorbing material.

4. The apparatus of claim 3 wherein the optical elements comprise a graded index lens and a corner cube at the distal ends of the peripheral fibers.

5. The apparatus of claim 1 wherein some fibers are forward viewing and some fibers are side viewing.

6. The apparatus of claim 1 wherein the distal ends of at least some of the fibers are positioned at different lengths along the guidewire.

7. The apparatus of claim 1 wherein the OCDR comprises:
    a 2×2 fiber optic coupler having first, second, third, and fourth ports;
    a low coherence source connected to the first port;
    the multiplexer being connected to the second port;
    a reference arm connected to the third port;
    a detector unit connected to the fourth port.

8. The apparatus of claim 7 further comprising a display device connected to the detector unit.

9. The apparatus of claim 7 further comprising an optical circulator connected between the source and the first port of the coupler and also connected to the detector unit.

10. The apparatus of claim 9 wherein the detector unit comprises a pair of balanced detectors, one detector being connected to the optical circulator and the other detector being connected to the fourth port of the coupler.

11. The apparatus of claim 7 wherein the reference arm comprises a scanning reference mirror.

12. The apparatus of claim 11 wherein the scanning reference mirror comprises a rotating helix reference mirror.

13. The apparatus of claim 12 wherein the rotating helix reference mirror comprises a disk with a radius which varies from a first radius to a second radius over its entire circumference, and having a mirror surface around its circumference.

14. The apparatus of claim 7 wherein the reference arm comprises a piezomodulator and a stationary reference mirror.

15. The apparatus of claim 7 wherein the optical fibers are polarization maintaining (PM) fibers and the coupler is a PM coupler.

16. The apparatus of claim 15 wherein the source is a linearly polarized light source or an unpolarized light source and a linear polarizer following the source.

17. The apparatus of claim 16 further comprising a waveplate or faraday rotator in the reference arm.

18. The apparatus of claim 17 wherein the detector unit comprises a pair of detectors, and further comprising a polarization beamsplitter positioned before the detectors to split returning light into two orthogonal polarizations, each polarization being input into a corresponding detector.

19. The apparatus of claim 18 wherein the detector unit includes means for determining birefringence versus depth of a sample by ratioing output signals from the pair of detectors.

20. The apparatus of claim 19 wherein linearly polarized light in the sample arm is directed into a birefringent sample with its axis of polarization at about 45° relative to the fast axis of the sample.

21. The apparatus of claim 20 further comprising a quarter wave plate placed at the distal end of each of the fibers to cause light incident onto the sample to be circularly polarized.

22. A guidewire optical sensing apparatus, comprising:
a single mode optical fiber having a distal and proximal end;
a body of x-ray absorbing material surrounding said fiber and forming a flexible guidewire with embedded fibers, the fiber directing light transmitted through the fiber to a surrounding area and collecting light reflected back from the surrounding area;
an optical coherence domain reflectometer (OCDR); and
an OCDR connected to the proximal end of said fiber.

23. A guidewire optical sensing apparatus, comprising:
a plurality of single mode optical fibers, each fiber having a distal and proximal end;
a body of x-ray absorbing material surrounding the fibers and forming a flexible guidewire with embedded fibers, the fibers directing light transmitted through the fiber to a surrounding area and collecting light reflected back from the surrounding area;
an optical coherence domain reflectometer (OCDR); and
an OCDR connected to the proximal end of each fiber of said plurality of single mode fibers to sequentially switch to each of the fibers.

* * * * *